United States Patent
Yu

(10) Patent No.: US 9,480,645 B2
(45) Date of Patent: *Nov. 1, 2016

(54) OMEGA-3 OIL CONTAINING OPHTHALMIC EMULSIONS

(75) Inventor: Zhi-Jian Yu, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1298 days.

This patent is subject to a terminal disclaimer.

(21) Appl. No.: 12/476,579

(22) Filed: Jun. 2, 2009

(65) Prior Publication Data

US 2010/0305045 A1    Dec. 2, 2010

(51) Int. Cl.
| | | |
|---|---|---|
| A61K 47/10 | (2006.01) | |
| A61K 9/00 | (2006.01) | |
| A61K 9/107 | (2006.01) | |
| A61K 47/44 | (2006.01) | |

(52) U.S. Cl.
CPC ........... *A61K 9/0048* (2013.01); *A61K 9/1075* (2013.01); *A61K 47/10* (2013.01); *A61K 47/44* (2013.01)

(58) Field of Classification Search
CPC ............................. A61K 47/44; A61K 47/10
See application file for complete search history.

(56) References Cited

U.S. PATENT DOCUMENTS

| | | | |
|---|---|---|---|
| 6,235,781 | B1 | 5/2001 | Weiner et al. |
| 6,506,412 | B2* | 1/2003 | Troyer et al. ................. 424/523 |
| 6,653,327 | B2 | 11/2003 | Majeed et al. |
| 2002/0032171 | A1 | 3/2002 | Chen et al. |
| 2004/0067244 | A1 | 4/2004 | Friedman |
| 2006/0015710 | A1 | 1/2006 | Natu |
| 2006/0182771 | A1* | 8/2006 | Dor et al. ..................... 424/400 |
| 2006/0251685 | A1 | 11/2006 | Yu et al. |
| 2007/0015692 | A1 | 1/2007 | Chang et al. |
| 2007/0015694 | A1 | 1/2007 | Chang et al. |
| 2007/0015710 | A1 | 1/2007 | Chang et al. |
| 2008/0299206 | A1 | 12/2008 | Lee et al. |

FOREIGN PATENT DOCUMENTS

| | | |
|---|---|---|
| EP | 1985298 A1 | 10/2008 |
| WO | WO0128555 A1 | 4/2001 |
| WO | WO029667 A2 | 2/2002 |
| WO | WO03063826 A | 8/2003 |
| WO | WO2006050836 A2 | 5/2006 |
| WO | WO2007008894 A2 | 1/2007 |
| WO | WO2007016073 A1 | 2/2007 |
| WO | WO2010070664 A1 | 6/2010 |

OTHER PUBLICATIONS

Abraham M.H., et al., "Draize Rabbit Eye Test Compatibility with Eye Irritation Thresholds in Humans: A Quantitative Structure-Activity Relationship Analysis," Toxicological Sciences, 2003, vol. 76 (2), pp. 384-391.
Fahr A., et al., "Drug Delivery Strategies for Poorly Water-Soluble Drugs," Expert Opinion on Drug Delivery, 2007, vol. 4 (4), pp. 403-416.
Gettings S.D., et al., "A Comparison of Low Volume, Draize and in Vitro Eye Irritation Test Data III Surfactant-based Formulations," Food and Chemical Toxicology, 1998, vol. 36 (3), pp. 209-231.
International Search Report for Application No. PCT/US2010/037070, mailed on Jan. 17, 2011, 4 pages.
International Search Report for Application No. PCT/US2010/037072, mailed on Sep. 15, 2010, 4 pages.
Majeed M., at al., "Currying Skin Health with Multifunctional Curcuminoids," Household and Personal Care Today, 2007, 3 pages.
Manach C., et al., "Polyphenols: Food Sources and Bioavailability," American Journal of Clinical Nutrition, 2004, vol. 79 (5), pp. 727-747.
Sabinsa Corporation "Certificate of Composition: Tetrahydro Curcuminoids OG," 1 page.
Sabinsa Corporation "Finished Product Specification: Tetrahydro Curcuminoids OG," 1 page.
Sabinsa Corporation "Material Data Sheet; Tetrahydrocurcuminoids OG," Nov. 2007, Ref No. MS-2023-01, 3 pages.
Sabinsa Corporation "Product Data Sheet; Tetrahydrocurcuminoids OG," 1 page.
Sabinsa Cosmetics Tetrahydrocurcuminoids "Innovating Natural Actives for Your Brands," 1 page.
Tetrahydrocurcuminoids (OG) slides presentation 10 pages.
International Search Report for Application No. PCT/US2010/037077, mailed on Oct. 14, 2010, 4 pages.
Tamilvanan S., et al., "The Potential of Lipid Emulsion for Ocular Delivery of Lipophilic Drugs," European Journal of Pharmaceuticals and Biopharmaceutics, 2004, vol. 58 (2), pp. 357-368.
S.C. Dinda et al., "Enhancement of Skin Permeation of Ibuprofen from Ointments and Gels by Sesame Oil, Sunflower Oil, and Oleic Acid", Indian J Pharm Sci. 2006; (68) pp. 313-316.
D.A. Schaumberg et al., "Prevalence of Dry Eye Syndrome Among US Women", American Journal of Ophthalmology Aug. 2003 pp. 318-326.
H.D. Perry et al., "Evaluation of Topical Cyclosporine for the Treatment of Dry Eye Disease", Arch Ophthalmol. Aug. 126 (8) pp. 1046-1050.

* cited by examiner

*Primary Examiner* — Zohreh Fay
(74) *Attorney, Agent, or Firm* — Abbott Medical Optics Inc.

(57) ABSTRACT

Disclosed herein are non-irritating ophthalmic emulsion compositions useful for treating ocular disorders including dry eye. More specifically, the ophthalmic compositions disclosed herein combine a high HLB surfactant and a low HLB surfactant together with an omega-3 fatty acid-containing oil having non-polar aliphatic side chains to form a therapeutic non-irritating eye drop.

12 Claims, 3 Drawing Sheets

US 9,480,645 B2

OMEGA-3 OIL CONTAINING OPHTHALMIC EMULSIONS

CROSS REFERENCE TO RELATED APPLICATIONS

Not applicable.

FIELD OF INVENTION

Disclosed herein are oil-in-water emulsions suitable for ophthalmic use. More specifically, the oil-in-water emulsions disclosed herein are useful as artificial tears and therapeutic agent delivery solutions.

BACKGROUND OF THE INVENTION

Oil-in-water emulsions generally comprise an aqueous phase having suspended therein discrete oil droplets (particles) surrounded by a layer of at least one water soluble surfactant. Emulsion stability is largely determined by particle size; oil-in-water-emulsions having particle sizes that exceed 1 µm in diameter tend to be less stable and undergo creaming, coagulation and phase separation upon storage. Therefore, for most applications it is desirable to reduce particle size which generally results in significant increases in aqueous phase surfactant concentration. The smaller the particle size, the greater the combined particle surface area resulting in a need for more surfactant in the aqueous phase, thus more free surfactant in solution.

Oil-in-water emulsions have a wide rage of ophthalmic applications including preparing solutions useful for treating storing and cleaning contact lenses, providing demulcents and lubricants and acting as carriers for therapeutic compositions. Ophthalmic emulsions may be specialized or multipurpose solutions. Examples of specialized ophthalmic solutions include treatments for keratoconjunctivitis sicca (dry eye). Dry eye results from evaporation of naturally occurring water from the eye surface. Dry eye treatment compositions generally comprise oil-in-water emulsions that restore the eye's natural aqueous layer and provide an oil layer over the newly added aqueous layer to prevent further evaporation. In other embodiments dry eye treatment compositions are emulsions that also contain hydrophobic therapeutic agents such as cyclosporine and/or a variety of demulcents such as carboxymethyl cellulose, hydroxyproyl cellulose, hyaluronic acid, polyvinyl alcohol, polysorbates, providone and other. Still other dry eye specialty ophthalmic solutions compositions may include at lease one therapeutic agent such as cyclosporine A.

However, all ophthalmic compositions comprising an oil-in-water emulsion used directly in the eye, whether as a dedication artificial tear or dry eye therapeutic, achieve maximum efficacy when the oil phase spreads evenly and freely over the eye surface. Moreover, ophthalmic emulsions should be relatively stable on storing to permit convenient frequent application to the eye. However, many oil-in-water emulsions contain excessive amounts of free hydrophilic surfactant. The free hydrophilic surfactant can wash away the tear film's natural lipid component and damage the mucin layer covering the cornea or conjunctiva thus exacerbating dry eye. Therefore, oil-in-water emulsion having a small particle size (average less than 1 µm in diameter) that contain non-irritating amounts of eye-damaging free hydrophilic surfactant in the aqueous phase are desirable

BRIEF SUMMARY OF THE INVENTION

Provided herein are ophthalmic oil-in-water emulsion composition comprising ophthalmically acceptable omega-3 fatty acid-containing oil wherein the oil comprises only aliphatic side chains free of polar pendent groups, a hydrophilic surfactant having an HLB value greater than 8 (high HLB component), hydrophobic non-co-block surfactant having an HLB value less than 8 (low HLB component) (collectively referred to as the "surfactant system"), water; and wherein the oil-in-water emulsion composition has an average particle size less than 1 µm in diameter.

The surfactant system comprises at least two surfactants; the first surfactant has a hydrophile to lipophile balance (HLB) of greater than 8 and a second surfactant having a HLB value of less than 8 wherein the ratio of hydrophilic surfactant to hydrophobic surfactant is approximately 10 to 0.5, alternatively 10 to 1, alternatively 9 to 1, alternatively 8 to 1, alternatively 7 to 1, alternatively 6 to 1, alternatively 5 to 1, alternatively 4 to 1, alternatively 3 to 1, alternatively 2 to 1, alternatively 1 to 1, and all fractions and intermediate ratios included in the broader range of from approximately 10 to approximately 0.5.

In one embodiment the surfactant system's HLB ratio of high HLB to low HLB component comprises at least one surfactant having an HLB between 8.0 and 25.0 and at least one other surfactant having an HLB between 7.9 and 1.0.

In another embodiment the surfactant system's HLB ratio of high HLB component to low HLB component is 10.0 to 4.9.

In another embodiment the surfactant system's HLB ratio of high HLB component to low HLB component is 14.5 to 4.9.

In another embodiment the surfactant system's HLB ratio of high HLB component to low HLB component is 10.0 to 2.0.

In another embodiment the surfactant system's HLB ratio of high HLB component to low HLB component is 14.5 to 2.0.

In yet another embodiment the high HLB surfactant is Lumulse® GRH 40 or Lumulse® GRH 25 and the low HLB surfactant is Brij 72 or Brij 93.

In one embodiment the omega-3 fatty acid-containing oil is from a botanical source selected from the group consisting of Chia (chia sage or *Salvia hispanica*), Kiwifruit (Chinese gooseberry or *Actinidia chinensis*), Perilla (shiso or *Perilla frutescens*) Flax seed (linseed or *Linum usitatissimum*), Lingonberry (Cowberry or *Vaccinium vitis*-idaea), Camelina (Gold-of-pleasure or *Camelina sativa*), Purslane (*Portulaca* or *Portulaca oleracea*) and Black Raspberry (*Rubus occidentalis*), omega-6 or omega-9 fatty acid is a plant derived oil or fish oil.

In another embodiment the omega-3 fatty acid-containing oil is from cold water fish having polar alkyl side chains and include cod liver oil, salmon oil, anchovy oil and tuna oil.

The oil-in-water, non-irritating ophthalmic compositions disclosed herein can also include excipients including, but not limited to buffers, microbicides, demulcents, viscosity modifying agents, metal salts, emulsion stabilizers and therapeutic agents.

In one embodiment an ophthalmic oil-in-water emulsion composition is provided that comprises an average particle size less than 1 µm, least one ophthalmically acceptable omega-3 fatty acid-containing oil, a hydrophilic surfactant having an HLB value between approximately 10 and 14 and a hydrophobic non-co-block surfactant having an HLB value between approximately 4 and 6.

In another embodiment an ophthalmic oil-in-water emulsion composition is provided that comprises ophthalmic oil-in-water emulsion composition comprising an average particle size less than 0.6 µm and wherein the oil-in-water emulsion consists essentially of water, at least one ophthalmically acceptable omega-3 fatty acid-containing oil, a hydrophilic surfactant having an HLB value between approximately 12 and 14 and a hydrophobic non-co-block surfactant having an HLB value between approximately 4 and 5.

In yet another embodiment an ophthalmic oil-in-water emulsion composition is provided that comprises an ophthalmic oil-in-water emulsion composition comprising an average particle size less than 0.6 μm and wherein the oil-in-water emulsion consists essentially of water, at least one ophthalmically acceptable omega-3 fatty acid-containing oil and a hydrophilic surfactant having an HLB value between approximately 10 and 11, a hydrophobic non-co-block surfactant having an HLB value between approximately 4 and 5.

In still another embodiment an ophthalmic oil-in-water emulsion composition is provided that comprises an ophthalmic oil-in-water emulsion composition comprising an average particle size less than 0.6 μm and wherein the oil-in-water emulsion consists essentially of water, flax seed, a hydrophilic surfactant consisting of Lumulse® GRH 25 and a hydrophobic non-co-block surfactant consisting of Brij 93.

A further embodiment includes an ophthalmic oil-in-water emulsion that comprises an ophthalmic oil-in-water emulsion composition comprising an average particle size less than 0.6 μm and consists essentially of flax seed oil, a hydrophilic surfactant having consisting of Lumulse® GRH 40 or Lumulse® GRH 25, a hydrophobic non-co-block surfactant consisting of Brij 93 or Brij 72 and wherein in the ophthalmic composition further comprises an amount of cyclosporine A effective to relieve dry eye symptoms.

DEFINITION OF SELECTED TERMS

Figure 1:
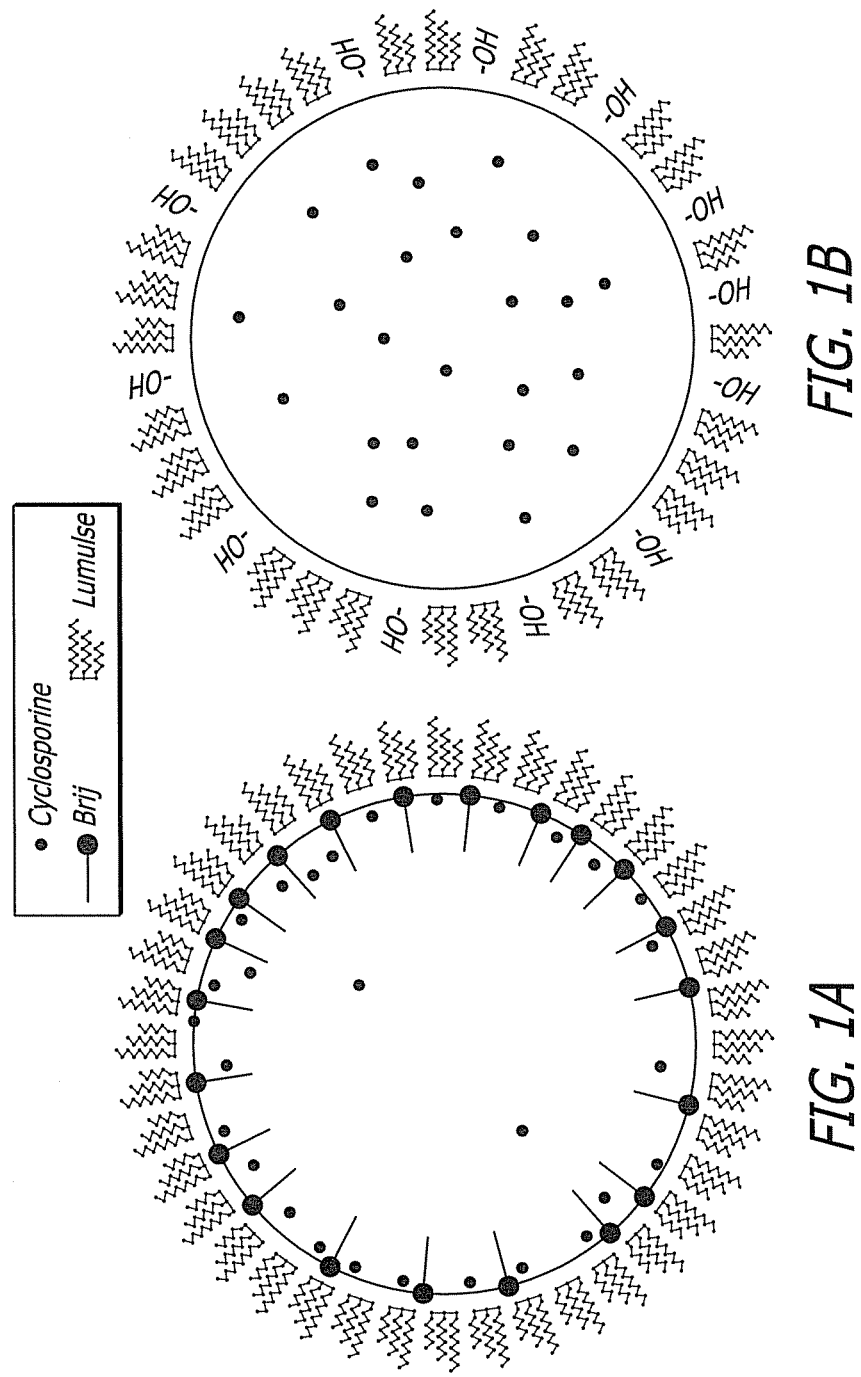
FIG. 1A depicts the hydrophobic therapeutic distribution in an oil particle made in accordance with the present teachings.
FIG. 1B depicts the hydrophobic therapeutic distribution in an oil particle made in accordance with the prior art

For the avoidance of doubt, the following terms as used herein are defined as follows. Words or terms not specifically defined shall have the ordinary meaning as known to those skilled in the art of pharmaceutical formulations, emulsion chemistry or opthalmology The term "artificial tears" as used herein means non-irritating lubricant eye drops used to treat the dryness and irritation associated with deficient tear production including dry eyes. They are also used to moisten contact lenses and in eye examinations.

The term "clear viscous gel" as used herein refers to a semisolid preparation that is clear and does not flow.

The term "cleaning" as used herein includes the loosening and/or removal of deposits and other contaminants from a contact lens with or without digital manipulation and with or without an accessory device that agitates the composition.

The term "demulcent" is used in the usual sense and refers to an agent that relieves irritation of inflamed or abraded lens and/or eye surfaces.

The term "emulsion" is used in its customary sense to mean a kinetically stable but thermodynamically unstable homogenous mixture of two liquids which do not normally mix such as oil and water.

The term "multi-purpose composition," as used herein, is an ophthalmic solution useful for performing at least two functions, such as cleaning, rinsing, disinfecting, rewetting, lubricating, disinfecting, conditioning, soaking, storing and otherwise treating a contact lens, while the contact lens is out of the eye. Such multi-purpose compositions preferably are also useful for re-wetting and cleaning contact lenses while the lenses are in the eye. Products useful for re-wetting and cleaning contact lenses while the lenses are in the eye are often termed re-wetters or "in-the-eye"

The term "non-irritating" as used herein is defined as a composition that does not result in subjective discomfort in the majority of users when applied directly or indirectly to the eye surface. It is understood that the condition of the user's eye and idiopathic sensitivity to one or more of the compositions' ingredients may result in irritation or discomfort in some users. However, as used herein "non-irritating" refers to the overall reaction the majority of normal users will experience immediately after, and for a reasonable period of time thereafter, application to the eye surface.

The term "non-polar oil" as used herein refers to a pharmaceutically acceptable plant or fish oil that do not have hydroxyl groups pendant to the side chains such as, but not limited to castor oil, which is expressly excluded from the present invention. Moreover, mineral oils, although technically are non-polar oils, are not plant or fish derived and therefore are not included with the definition of "non-polar oil" as used herein and are expressly excluded form the present invention.

The term "ophthalmically acceptable" as used herein means and constituent of the oil-in-water compositions described herein that does not cause injury or prolonged discomfort to the eye of the average user.

The term "particle" as used herein refers to a spherical oil droplet suspended in the aqueous phase of an oil-in-water emulsion.

The term "paste" as used herein refers to a semisolid preparation which does not flow.

The term "re-wetting" as used herein refers to the addition of liquid over at least a part, for example, at least a substantial part, of at least the anterior surface of a contact lens.

The term "stable" is used in its customary sense and means the absence of coagulation, creaming, and phase separation for at least one month. "Relatively stable" refers to an oil-in-water emulsion that requires occasional shaking prior to use but exhibits al of the other beneficial and desirable qualities described herein.

The term "surface active agent" generally refers to a surfactant, detergent or emulsifier as defined below. However, as used herein "surface active agent" refers specifically to the active lens cleaning component of a multi-purpose solution. However, the term "surface active agent' used in that context is not intended to limit the contribution the surface active agent may make to other aspects of the composition such as emulsification, stability and enhancing active agent solubility.

The term "surfactant" refers to a substance which aids the formation of an emulsion such and includes emulsifiers, detergents and other surface active agents. The terms "emulsifier," "surface active agent," "detergent" and "surfactant" are used interchangeably herein. In the context described herein, surfactant system means at least two surfactants, one having and HLB greater than 8 and the other having an HLB less than 8.

DETAILED DESCRIPTION OF THE INVENTION

Provided herein are ophthalmic compositions comprising oil-in-water emulsions that are non-irritating when applied to the eye. The ophthalmic compositions provided herein are useful for lubricating the eye surface (artificial tears) and for treating or relieving the symptoms associated with a large range of eye conditions ranging from occasional sore and tiered eyes to inflamed, infected and diseased eyes. Such eye conditions are often treated using topically applied eye drops containing therapeutic agents.

Successful ophthalmic emulsion solution compositions need to possess two important properties. Ophthalmic emulsion solutions need to relatively stable, that is once formed the emulsion needs to retain its initial properties without separating, coagulating or creaming, although occasional shaking prior to use is acceptable for many applications. Ophthalmic emulsions that solidity (cream) or coagulate are not solutions and therefore, while potentially useful as ointments, are not acceptable as ophthalmic multi-use solutions. Ophthalmic emulsion solutions that separate need to be shaken regularly prior to use with; this step may be inadvertently forgotten resulting in the user applying an ineffective or irritating solution to the eye or lens.

Secondly, ophthalmic solution compositions must be non-irritating when applies to the eye. Irritation is generally caused by excessive lipophilic surfactant being present in the aqueous phase. When the ophthalmic composition having excessive aqueous phase lipophilic surfactant is applied to the eye, the surfactant washes away the tear film's natural lipid component and damages the mucin layer covering the cornea or conjunctiva thus irritating the eye and/or exacerbating dry eye syndrome.

However, making a relatively stable, non-irritating ophthalmic composition solution remains a challenge and has resulted in a number of less than completely satisfactory compromises. This is especially true for multi-use solutions are concerned where the need to balance lens cleaning efficacy with user comfort can be especially challenging. Without wishing to be bound to or limited by this theory, the present inventor has observed that oil-in-water emulsion stability and flow characteristics are at least in part determined by particle size. Thus the smaller the particle size, the inherently more stable the emulsion becomes and the more flowable (spreading evenly over the eye surface). In one embodiment the emulsions disclosed herein have a particle size average less than 1 μm in diameter, in another embodiment the particle size average is less than 0.8 μm in diameter; in another embodiment the particle size average is less than 0.6 μm in diameter; in another embodiment the particle size average is less than 0.4 μm; in another embodiment the particle size average is less than 0.2 μm in diameter; in another embodiment the particle size average is less than 0.1 μm in diameter.

Prior art oil-in-water emulsions achieved increased stability and smaller particle size by increasing the water soluble (higher HLB) surfactants concentration in the emulsion. However, while this practice did decrease particle size and thus increase stability; it also increased the amount of free hydrophilic surfactant present in the ophthalmic composition's aqueous phase thus irritating the eye.

Surprisingly, the present inventor has discovered that by closely matching the surfactant system with the oil component, the adverse effects resulting from excessive amounts of free surfactant can be avoided while simultaneously achieving the desired particle size and thus improving the therapeutic emulsion's overall performance. FIG. 1 depicts one embodiment described herein (FIG. 1A) compared with a prior art embodiment (FIG. 1B). FIG. 1 is not necessarily drawn to scale but serves to depict one aspect of how the present emulsions may achieve their desirable properties over the prior art. Note that prior art embodiment combines the single detergent Lumulse® and a polar oil, castor oil, to achieve a desired emulsion composition. However, the presence of hydroxyl groups on the oil droplet surface reduces the number of sites where the aqueous phase surfactant Lumulse® can interact with the droplet compared with a representative embodiment made according to the present teachings comprised of a non-polar oil and the detergent system described herein. It can be seen in FIG. 1A that proportionally more aqueous phase detergent (in this example Lumulse®) is sequestered on the oil droplet's outer surface with emulsion compositions made in accordance with these teaching than in the prior art composition (FIG. 1B) resulting in significantly less free surfactant in the aqueous phase and therefore a less irritating ophthalmic solution.

As mentioned briefly above, equally surprising was the effect of choosing the optimal surfactant system to pair with the oil component of the present therapeutic ophthalmic emulsion. The present inventor surprisingly discovered that combining an oil soluble/water insoluble surfactant (hydrophobic surfactant) with a hydrophilic surfactant the total amount of free hydrophilic surfactant in the aqueous phase was remarkably reduced; but only in combination with a non-polar oil. In fact, the present inventor discovered that merely adding a hydrophobic surfactant to the prior art combination of castor oil and a hydrophilic surfactant actually increased the amount to free hydrophilic surfactant in the aqueous phase and thus exacerbated eye irritation. As will be demonstrated in the experimental section included herein, this increase in free hydrophilic surfactant in the aqueous phase results from a significant increase in particle size when a polar oil is used in combination with the surfactant systems disclosed herein, which would be completely unexpected given the significant reduction in particle size when the surfactant systems taught herein are used with non-polar oils (See FIG. 2A) and FIG. 2B which represents the prior art embodiment.

Figure 3:
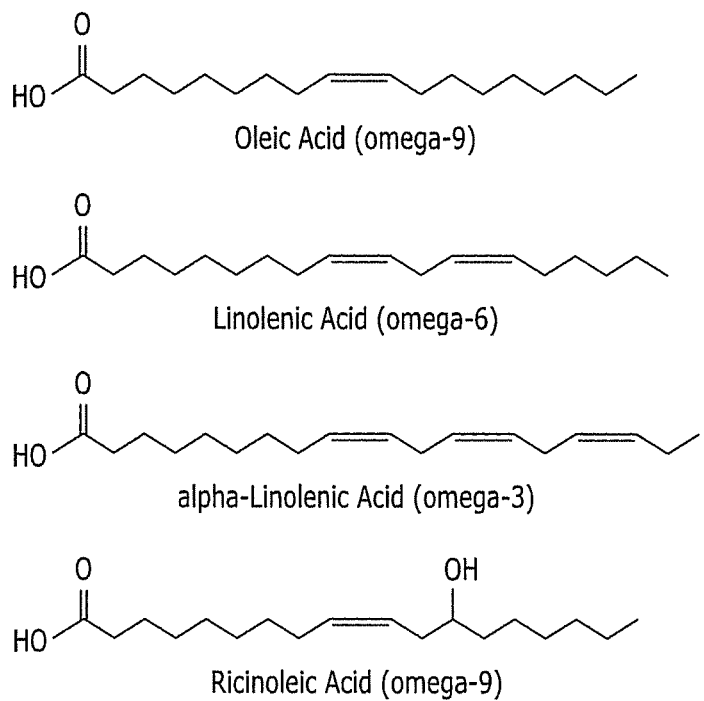
FIG. 3 depicts the molecular structures of the omega fatty acid side chains associated with the non-polar oils described herein and contrasted to the expressly excluded polar oil side chain of castor oil.

Provided herein are, non-irritating oil-in-water multi-use ophthalmic emulsions comprising oil particles suspended in an aqueous phase wherein the oil particle size averages is less than 1 μm in diameter. The oil-in-water ophthalmic emulsions presently disclosed comprise oils having non-polar aliphatic or alkyl chains such as, but not limed to the family of unsaturated fatty acids known as omega-3, -6 or -9 oils (See FIG. 3 and FIG. 4). The oil-in-water emulsions include a surfactant system comprising at least one hydrophilic and at least one hydrophobic surfactant. Additionally the oil-in-water emulsions may include other excipients such as, but not limited to, demulcents, lubricants, viscosity modifiers, tonicity enhancers, metallic salts, buffers and therapeutic compositions such as cyclosporine A.

The non-polar pharmaceutically acceptable oils useful for making the oil-in-water therapeutic emulsions described herein include plant-derived unsaturated fatty acids having at least one carbon-carbon double bond in their non-polar aliphatic or alkyl side chains. Particularly desirable examples include the omega fatty acids. Omega-3 fatty acids have the carbon-carbon double bond at the n−3 position from the methyl end of the fatty acid; omega-6 fatty acids have a carbon-carbon double bond in the n−6 position; that is, the sixth bond from the end of the fatty acid and omega-9 fatty acids which have in common a carbon-carbon double bond in the n−9 position; that is, the ninth bond from the end of the fatty acid.

Table 1 lists non-limiting representative omega-3 fatty acids that may be present in the non-polar oils used in the present oil-in-water emulsions.

TABLE 1

Several different names for the most common n-3 fatty acids found in nature.

| Common name | Lipid name | Chemical name |
| --- | --- | --- |
| | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (STD) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Docosapentaenoic acid (DPA), Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid | 24:5 (n-3) | all-cis-9,12,15,18,21-docosahexaenoic acid |
| Tetracosahexaenoic acid (Nisinic acid) | 24:6 (n-3) | all-cis-6,9,12,15,18,21-tetracosenoic acid |

Figure 4:
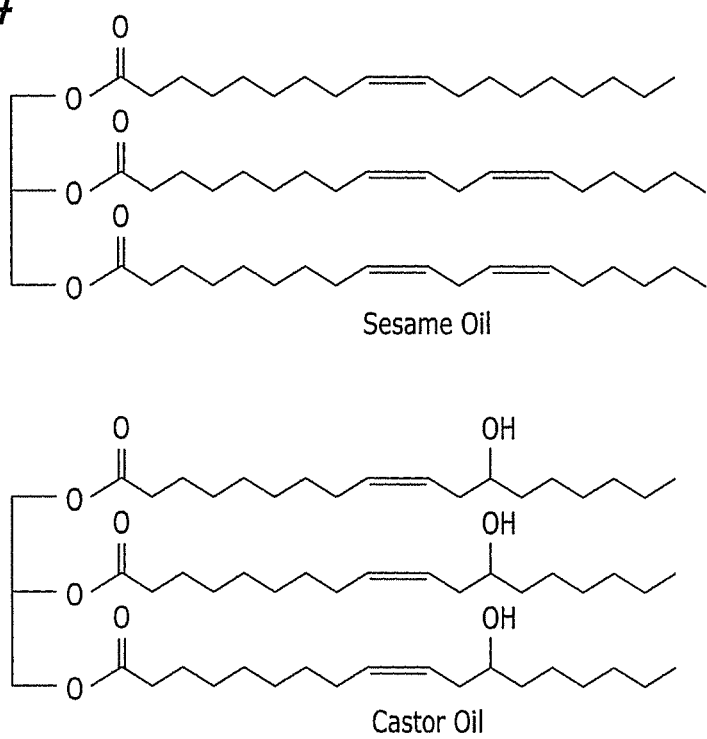
FIG. 4 depicts two fatty acids of FIG. 3 as naturally occurring triglycerides.

As depicted in FIG. 4 oils are often a blend of more than one fatty acid type, for example in one embodiment described herein the oil used for the oil-in-water emulsion is sesame seed oil. Sesame oil has about 43% each of linoleic acid (an omega 6 fatty acid) and oleic acid (an omega 9 fatty acid) (see for example Dina S C et al. *Enhancement of skin permeation of ibuprofen from ointments and gels by sesame oil, sunflower oil and oleic acid*. Indian J Pharm Sci. 2006; 68:313-316. The entire contents of which are incorporated herein by reference). However neither linoleic acid nor oleic acid have a hydroxyl group on the side chain such as castor oil does and therefore, for the purposes described herein, sesame seed oil is a non-polar oil as that term is used herein. Other suitable non-limiting examples of plant-derived omega fatty acid-containing oils include cherry kernel oil, pumpkin seed oil, hemp seed oil, flax seed oil, perilla seed oil, and blackcurrant seed oil. However, neither castor oil (oils having a polar aliphatic or alkyl chains generally) nor mineral oil (completely non-polar oils) is suitable for use in preparing the oil-in-water compositions described herein and both castor oil and mineral oil expressly excluded from the appended claims.

Particularly useful oils include the omega-3 fatty acid-containing botanical oils selected from the group consisting of Chia (chia sage or *Salvia hispanica*), Kiwifruit (Chinese gooseberry or *Actinidia chinensis*), Perilla (shiso or *Perilla frutescens*) Flax seed (linseed or *Linum usitatissimum*), Lingonberry (Cowberry or *Vaccinium vitis*-idaea), Camelina (Gold-of-pleasure or *Camelina sativa*), Purslane (*Portulaca* or *Portulaca oleracea*) and Black Raspberry (*Rubus occidentalis*) and omega-3 fatty acid-containing oil from cold water fish having polar alkyl side chains and selected from the group consisting of cod liver oil, salmon oil, anchovy oil and tuna oil.

The surfactant system used in accordance with the teaching herein comprises at least two surfactants; the first surfactant has a HLB of greater than 8 (hydrophilic surfactant) and a second surfactant having a HLB of less than 8 (hydrophobic surfactant) wherein the ratio of hydrophilic surfactant to hydrophobic surfactant is approximately 10 to 0.5, alternatively 10 to 1, alternatively 9 to 1, alternatively 8 to 1, alternatively 7 to 1, alternatively 6 to 1, alternatively 5 to 1, alternatively 4 to 1, alternatively 3 to 1, alternatively 2 to 1, alternatively 1 to 1, and all fractions and intermediate ratios included in the broader range of from approximately 10 to 0.5.

As is well known in the art, the terms "hydrophilic (hydrophile)" and "hydrophobic (lipophile)" are relative terms. To function as a surfactant, a compound must necessarily include polar or charged hydrophilic moieties as well as non-polar hydrophobic (lipophilic) moieties; i.e., a surfactant compound must be amphiphilic. An empirical parameter commonly used to characterize the relative hydrophilicity and hydrophobicity of non-ionic amphiphilic compounds is the "HLB" value. Surfactants with lower HLB values are more hydrophobic, and have greater solubility in oils, whereas surfactants with higher HLB values are more hydrophilic, and have greater solubility in aqueous solutions.

Table 2 provides a general guide to selecting surfactants based on HLB values.

| HLB range | Application |
| --- | --- |
| 3-6 | W/O emulsions |
| 7-9 | Wetting |
| 8-18 | O/W emulsions |
| 3-15 | Detergency |
| 15-18 | Solubilization |

Using HLB values as a rough guide, hydrophilic surfactants are generally considered to be those compounds having an HLB value greater than about 10, as well as anionic, cationic, or zwitterionic compounds for which the HLB scale is not generally applicable. Similarly, hydrophobic surfactants are compounds having an HLB value less than about 8. It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value (Schoft, J. Pharm. Sciences, 79(1), 87-88 (1990)). Likewise, for certain polypropylene oxide containing block copolymers (poloxamers, available commercially as Pluronic®. surfactants, BASF Corp.), the HLB values may not accurately reflect the true physical chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or hydrophobicity for use in the present invention, as described herein. See Table 3 below for non-limiting examples.

The carrier described herein includes at least one hydrophilic surfactant. The hydrophilic surfactant can be any surfactant suitable for use in pharmaceutical compositions. Suitable hydrophilic surfactants can be anionic, cationic, zwitterionic or non-ionic, although non-ionic hydrophilic surfactants are presently preferred. Preferably, the carrier includes a mixture of two or more hydrophilic surfactants, more preferably two or more non-ionic hydrophilic surfactants. Also preferred are mixtures of at least one hydrophilic surfactant, preferably non-ionic, and at least one hydrophobic surfactant.

The choice of specific surfactants should be made keeping in mind the particular triglycerides and optional therapeutic agents to be used in the composition, and the range of polarity appropriate for the chosen therapeutic agent. With these general principles in mind, a very broad range of surfactants is suitable for use in the present invention. Providing the surfactant system in accordance with the teaching herein comprises at least two surfactants; the first surfactant has a HLB value of greater than 8 and a second surfactant having a HLB of less than 8. In one embodiment the surfactant system's HLB ratio of high HLB to low HLB component comprises at least one surfactant having an HLB between 8.0 and 25.0 and at least one other surfactant having an HLB between 7.9 and 1.0. In another embodiment the surfactant system's HLB ratio of high HLB component to low HLB component is 10.0 to 4.9. In another embodiment the surfactant system's HLB ratio of high HLB component to low HLB component is 14.5 to 4.9. In another embodiment the surfactant system's HLB ratio of high HLB component to low HLB component is 10.0 to 2.0. In another embodiment the surfactant system's HLB ratio of high HLB component to low HLB component is 14.5 to 2.0.

Such surfactants can be grouped into the following general chemical classes detailed in the Tables herein. The HLB values given in Table 3 below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable. It should be emphasized that the invention is not limited to the surfactants in the Tables, which show representative, but not exclusive, lists of available surfactants.

TABLE 3

HLB Values for Representative Surfactants

| Surfactant | Synonym | HLB |
|---|---|---|
| 2,4,7,9-Tetramethyl-5-decyne-4,7-diol | | 4.0 |
| PEG-block-PPG-block-PEG, MN 1100 | | 4.0 |
| PEG-block-PPG-block-PEG, MN 2000 | | 4.0 |
| PEG-block-PPG-block-PEG, MN 2800 | | 4.0 |
| PEG-block-PPG-block-PEG, MN 4400 | | 4.0 |
| Ethylenediamine tetrakis(PO-b-EO) tetrol, MN 3600 | | 4.0 |
| Ethylenediamine tetrakis(EO-b-PO) tetrol, MN 7200 | | 4.0 |
| Ethylenediamine tetrakis(EO-b-PO) tetrol, MN 8000 | | 4.0 |
| Igepal ® CA-210 | Polyoxyethylene(2) isooctylphenyl ether | 4.3 |
| Sorbitan monooleate | Span ® 80 | 4.3 |
| PPG-block-PEG-block-PPG, MN 3300 | | 4.5 |
| Igepal CO-210 | Polyoxyethylene(2) nonylphenyl ether | 4.6 |
| Sorbitan monostearate | Span ® 60 | 4.7 |
| Brij ® 92/93 | Polyoxyethylene(2) oleyl ether | 4.9 |
| Brij ® 72 | Polyoxyethylene(2) stearyl ether | 4.9 |
| Brij ® 52 | Polyoxyethylene(2) cetyl ether | 5.3 |
| Sorbitan monopalmitate | Span ® 40 | 6.7 |
| Merpol ® A surfactant | | 6.7 |
| 2,4,7,9-Tetramethyl-5-decyne-4,7-diol ethoxylate | | 8.0 |
| Triton ® SP-135 | | 8.0 |
| Sorbitan monolaurate | Span ® 20 | 8.6 |
| PEG-block-PPG-block-PEG, MN 5800 | | 9.5 |
| PPG-block-PEG-block-PPG, MN 2700 | | 9.5 |
| Brij ® 30 | Polyoxyethylene(4) lauryl ether | 9.7 |
| Igepal ® CA-520 | Polyoxyethylene(5) isooctylphenyl ether | 10.0 |
| Igepal ® CO-520 | Polyoxyethylene(5) nonylphenyl ether | 10.0 |
| Lumulse ® GRH-25 | Polyethylene Glycol Ester of Hydrogenated Castor Oil | 10.0 |
| Polyoxyethylene sorbitol hexaoleate | | 10.2 |
| Merpol ® SE surfactant | | 10.5 |
| Tween ® 85 | Polyoxyethylene(20) sorbitan trioleate | 11.0 |
| 8-Methyl-1-nonanol propoxylate-block-ethoxylate | | 11.0 |
| Polyoxyethylene sorbitan tetraoleate | | 11.4 |
| Triton ® X-114 | Polyoxyethylene(8) isooctylphenyl ether | 12.4 |
| Brij ® 76 | Polyoxyethylene(10) stearyl ether | 12.4 |
| Brij ® 97 | Polyoxyethylene(10) oleyl ether | 12.4 |
| Merpol ® OJ surfactant | | 12.5 |
| Brij ® 56 | Polyoxyethylene(10) cetyl ether | 12.9 |
| Merpol ® SH surfactant | | 12.9 |
| Tergitol ® NP-9 | Nonylphenol polyethylene glycol ether | 12.9 |
| 2,4,7,9-Tetramethyl-5-decyne-4,7-diol ethoxylate (5 EO/OH) | | 13.0 |

TABLE 3-continued

HLB Values for Representative Surfactants

| Surfactant | Synonym | HLB |
|---|---|---|
| Triton ® SP-190 | | 13.0 |
| Igepal ® CO-630 | Polyoxyethylene(9) nonylphenyl ether | 13.0 |
| Triton ® X-100 | Polyoxyethylene(10) isooctylphenyl ether | 13.5 |
| Lumulse ® GRH-40 | Polyethylene Glycol Ester of Hydrogenated Castor Oil | 13.5 |
| Igepal ® CO-720 | Polyoxyethylene(12) nonylphenyl ether | 14.2 |
| Polyoxyethylene(12) tridecyl ether | | 14.5 |
| Polyoxyethylene(18) tridecyl ether | | 14.5 |
| Igepal ® CA-720 | Polyoxyethylene(12) isooctylphenyl ether | 14.6 |
| Tween ® 80 | Polyoxyethylene(20) sorbitan monooleate | 14.9 |
| Tween ® 60 | Polyoxyethylene(20) sorbitan monostearate | 15.0 |
| PEG-block-PPG-block-PEG, MN 2900 | | 15.0 |
| PPG-block-PEG-block-PPG, MN 2000 | | 15.0 |
| Brij ® 78 | Polyoxyethylene(20) stearyl ether | 15.3 |
| Brij ® 98 | Polyoxyethylene(20) oleyl ether | 15.3 |
| Merpol ® HCS surfactant | | 15.5 |
| Tween ® 40 | Polyoxyethylene(29) sorbitan monopalmitate | 15.6 |
| Brij ® 58 | Polyoxyethylene(20) cetyl ether | 15.7 |
| Polyethylene-block-poly(ethylene glycol)Mn 2250 | | 16.0 |
| Tween ® 20 | Polyoxyethylene(20) sorbitan monolaurate | 16.7 |
| Brij ® 35 | Polyoxyethylene(23) lauryl ether | 16.9 |
| 2,4,7,9-Tetramethyl-5-decyne-4,7-diol ethoxylate (15 EO/OH) | | 17.0 |
| Igepal ® CO-890 | Polyoxyethylene(40) nonylphenyl ether | 17.8 |
| Triton ® X-405 | Polyoxyethylene(40) isooctylphenyl ether | 17.9 |
| Brij ® 700 | Polyoxyethylene(100) stearyl ether | 18.8 |
| Igepal ® CO-990 | Polyoxyethylene(100) nonylphenyl ether | 19.0 |
| Igepal ® DM-970 | Polyoxyethylene(150) dinonylphenyl ether | 19.0 |
| PEG-block-PPG-block-PEG, MN 1900 | | 20.5 |
| PEG-block-PPG-block-PEG, MN 8400 | | 24.0 |
| Ethylenediamine tetrakis(PO-b-EO) tetrol, MN 15000 | | 24.0 |
| PEG-block-PPG-block-PEG, average Mn ca. 14,600 | | 27.0 |

The following are registered trademarks:

Igepal® Rhodia Operations Societe Par Actions Simplifiee France 40 Rue De La Haie Coq Aubervilliers France 93306

Brij® ICI Americas Inc. Corporation By Merger With And Change Of Name From Delaware New Murphy Road And Concord Pike Wilmington Del. 19897

Merpol® Stepan Company Corporation By Assignment Delaware 22 West Frontage Road Northfield Ill. 60093

Lumulse® Lambent Technologies Inc. Corporation Georgia 2416 Lynndale Road Fernandina Beach Fla. 32024

Triton® X-100 is a registered trademark of Union Carbide and was purchased from Rohm & Haas Co Tween® ICI Americas Inc. Corporation By Merger With And Change Of Name From Delaware New Murphy Road And Concord Pike Wilmington Del.

The oil-in-water, non-irritating ophthalmic compositions disclosed herein can also include excipients including, but not limited to buffers, microbicides, demulcents, viscosity modifying agents, metal salts and therapeutic agents.

In one embodiment the viscosity modifying agent is selected from the group consisting of hyaluronic acid and salts thereof, polyvinylpyrrolidone (PVP), cellulose polymers, including hydroxypropyl methyl cellulose (HPMC), hydroxyethyl cellulose (HEC), ethyl hydroxyethyl cellulose, hydroxypropyl cellulose, methyl cellulose and carboxymethyl cellulose (CMC), dextran 70, gelatin, glycerine, polyethylene glycols, polysorbate 80, propylene glycol, povidone, carbomers (e.g. Carbopol®), polyvinyl alcohol, alginates, carrageenans, and guar, karaya, agarose, locust bean, tragacanth and xanthan gums.

In another embodiment the microbicide is a polymeric quaternary amine preservative selected from the group consisting of poly[dimethylimino-w-butene-1,4-diyl]chloride, alpha-[4-tris(2-hydroxyethyl)ammonium]dichloride (Polyquaternium 1®), poly(oxyethyl(dimethyliminio)ethylene dmethyliminio)ethylene dichloride (WSCP®), polyhexamethylene biguanide (PHMB).

EXAMPLES

Example 1

Comparison of Particle Size with Different Surfactant Systems

TABLE 4

Particle size as a function of surfactant system

| | % w/w | % w/w | % w/w | % w/w |
|---|---|---|---|---|
| Sesame oil | 2.5 | 2.5 | 2.5 | 2.5 |
| Lumulse GRH-40 | 1.5 | 1.0 | 1.0 | 0.5 |
| Brij 72 | | | 0.5 | 0.5 |
| Boric acid | 0.60 | 0.60 | 0.60 | 0.60 |
| Sodium borate decahydrate | 0.15 | 0.15 | 0.15 | 0.15 |
| NaCl | 0.40 | 0.40 | 0.40 | 0.40 |
| water | 94.85 | 95.35 | 94.85 | 95.35 |
| particle size (um) | 4.71 | 126.95 | 0.31 | 0.59 |

It can be seen from the data present in Table 4 that the particle size of a sesame oil in an oil-in-water emulsion decreases significantly when a low HLB value (hydrophobic) surfactant (HLB for Brij 72 is approximately 4.9) is added to the composition in combination with the higher HLB (HLB value for Lumulse® GRH-40 is approximately 13.5). Note that nearly twice as much hydrophilic surfactant is necessary to achieve a particle size less than 1 μm when used alone than when used in combination with a hydrophobic surfactant. The reduced particle size and lower concentration of hydrophilic surfactant in the composition results in less irritating and thus more efficacious ophthalmic compositions.

This Example 1 demonstrates an important aspect of the present teachings. The addition of an oil soluble/water insoluble surfactant (low HLB) to the oil phase of the oil-in-water emulsion, significantly reduces the amount of the water soluble (hydrophilic) surfactant (high HLB) in the aqueous phase making the ophthalmic solution less irritating.

Example 2

Therapeutic Agent Delivery

In another embodiment of the present teachings a therapeutic agent useful for treating eye disorders may be included in the ophthalmic oil-in-water emulsions described herein. Non-limiting examples of eye disorders treated with therapeutic-containing eye drops include, but are not limited to, dye eye, glaucoma, conjunctivitis, blepharitis, allergies, and infections. Useful therapeutic agents include, but are not limited to steroids (e.g. mydriatics, dexamethasone), antihistamines, sympathomimetics, beta receptor blockers, parasympathomimetics (e.g. pilocarpine), parasympatholytics (e.g. tropicamide or atropine), prostaglandins, non-steroidal anti-inflammatory drugs (NSAIDs) or topical anesthetics. Specific, non-limiting examples include, azelastine, bimatoprost, ciprofloxin, cyclosporine A, flurbiprofen, levocabastine, ofloxacin, pilocarpine, rapamycin (and other macrolide antibiotics), and timolol. However, many of the aforementioned therapeutics are highly hydrophobic and therefore are not effectively delivered to the eye using aqueous solutions. Therefore, oil-in-water emulsions were developed in order to more effectively solubilize hydrophobic agents and thus increase their deliverability to the eye. However, prior art hydrophobic therapeutic-containing oil-in-water emulsions often result sub-optimal topical delivery systems because the active therapeutic agent is distributed throughout the center of the oil particle and thus less easily delivered to the eye surface (see FIG. 1B). However, the therapeutic-containing oil-in-water emulsions described herein provide an oil particle where the hydrophobic therapeutic is sequestered around the particles' outer parameter and thus more accessible to interact with the eye surface forming a more efficient therapeutic delivery system as compared to the prior art.

In one specific, non-limiting example cyclosporine A (also spelled ciclosporin or cyclosporin) is the hydrophobic therapeutic agent delivered to the eye. Cyclosporine A is an immunosuppressant drug widely used in post-allogeneic organ transplant to reduce the activity of the patient's immune system and the risk of organ rejection. It has been studied in transplants of skin, heart, kidney, liver, lung, pancreas, bone marrow and small intestine. Initially isolated from a Norwegian soil sample, Cyclosporine A, the main form of the drug, is a cyclic nonribosomal peptide of 11 amino acids (an undecapeptide) produced by the fungus *Tolypocladium inflatum* Gams, and contains D-amino acids, which are rarely encountered in nature.

A specific, non-limiting example of an eye disorder treated in accordance with the teachings herein is dry eye syndrome using cyclosporine A. Dry Eye is a prevalent condition for which there is no cure, although symptoms may be relieved with proper diagnosis and treatment. The condition affects more than 3.2 million American women middle-aged and older alone (Schaumberg D A, Sullivan D A, Buring J E, Dana M R. *Prevalence of dry eye syndrome among US women*. Am J Opthalmol 2003 August; 136(2): 318-26). Contact lens wearers, computer users, patients who live and/or work in dry environments, and patients with autoimmune disease are all particularly susceptible to developing dry eye. Recently, cyclosporine has been shown to be efficacious in treating dry eye and is the primary active ingredient in a leading prior art therapeutic-containing oil-in-water emulsion. (See Perry H D et al. *Evaluation of topical cyclosporine for the treatment of dry eye disease*. Arch Opthalmol. 2008 August; 126(8): 1046-50.)

In order to relieve dry eye symptoms the ophthalmic composition must achieve three basic treatment goals. First it must be easily and conveniently applied directly to the eye surface such that the aqueous component of the emulsion restores the evaporating aqueous layer naturally present on the eye surface and the emulsion's oil phase should form a layer over the aqueous layer reducing or preventing further evaporation. Secondly, the oil-in-water emulsion should be relatively stable such that it does not separate into phases on storage although occasional shaking prior to use is acceptable for certain application (frequent need for shaking can be inadvertently forgotten by the user). Third, the oil-in-water emulsion must remain sufficiently liquid that it flows easily from a dropper or other applications and does not congeal or for a paste on storage. Therefore, the ideal ophthalmic oil-in-water emulsion used to treat dye eyes and other ophthalmic conditions need to be relatively stable, have acceptable flow characteristics, and be non-irritating to the eye.

Cyclosporine is a hydrophobic therapeutic agent that is insoluble in water and therefore must be solubilized prior to being administered to the eye. The prior art formulation uses castor oil to dissolve cyclosporine due to its high solubility in this polar oil. However, castor oil's polarity forms an emulsion having the cyclosporine sequestered near the oil particles' core and away from the particle surface as depicted in FIG. 2B. Consequently cyclosporine transfer to the conjunctiva and cornea tissue is inefficient.

Figure 2:
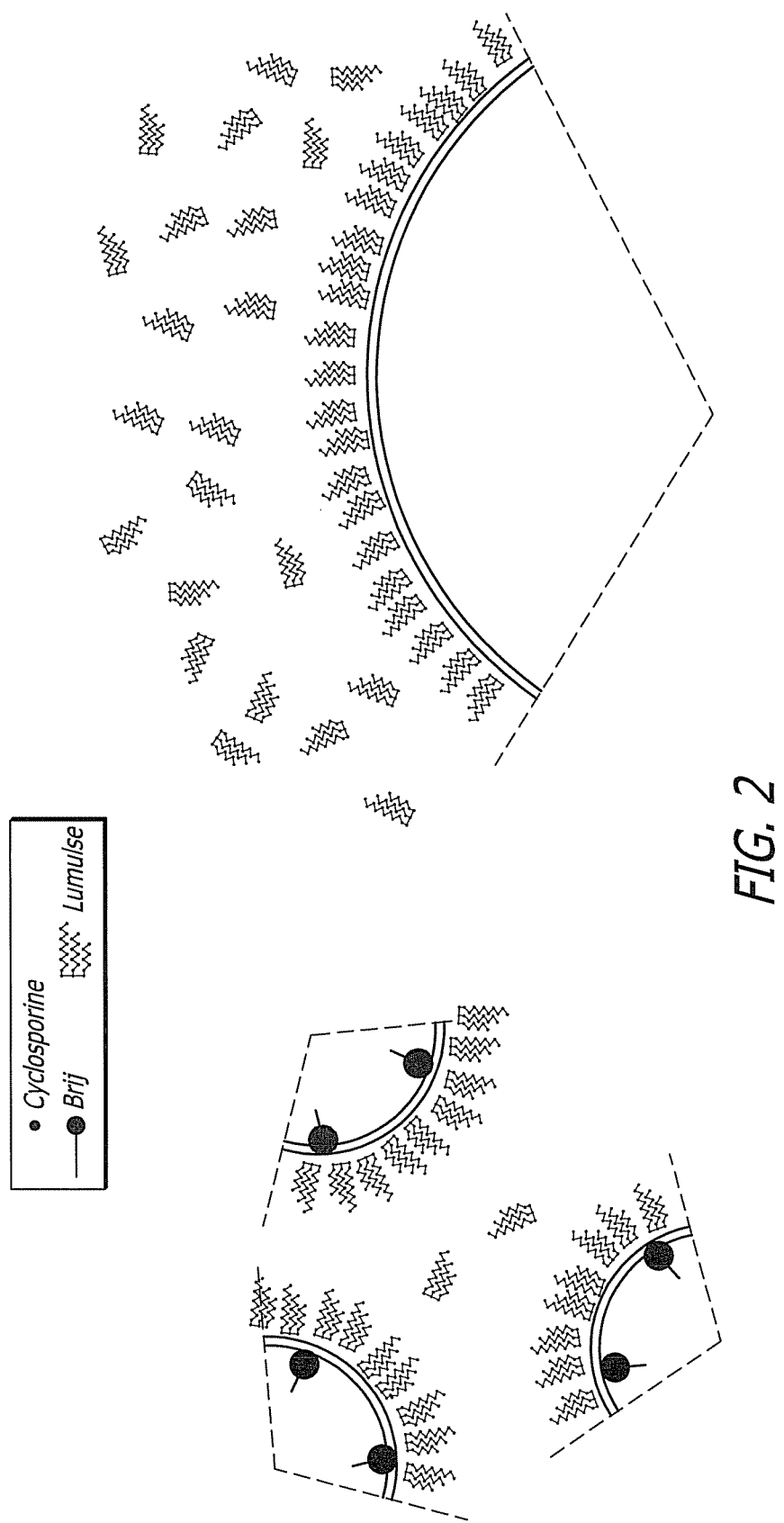
FIG. 2 depicts relative particle size based on surfactant types and the affect on surface area.

Cyclosporine has low solubility in non-polar oils such as sesame oil, soybean oil and flax seed oil. The present inventors discovered that adding a low HLB surfactant to the oil-cyclosporine mixture significantly increased the therapeutic agent's solubility and surprisingly increased cyclosporine delivery to conjunctiva and cornea tissue compared with castor oil containing emulsions (Table 4). FIG. 2A depicts a theoretical oil particle made in accordance with the teachings described herein. Note that the presence of the low HLB surfactant ("Brij") causes the cyclosporine (depicted in FIG. 2 as solid black dots) to be localized at the perimeter of the oil particle and thus more easily transferred to the eye surface as compared with FIG. 2B were the cyclosporine is sequestered near the oil particle central core.

TABLE 5

| Oils | Cyclosporine/oil weight ratio | Brij 93/oil weight ratio | Cyclosporine Solubility |
| --- | --- | --- | --- |
| Castor oil | 20% | 0 | soluble |
| Sesame oil | 5.6% | 0 | Insoluble |
| Sesame oil | 6.6% | 6.6% | soluble |
| Soybean oil | 5.6% | 0.0% | Insoluble |
| Soybean oil | 6.6% | 6.6% | soluble |
| Flax oil | 5.6% | 0 | Insoluble |
| Flax oil | 6.6% | 6.6% | soluble |

It is important to understand that merely adding Brij, or another low HLB surfactant to a castor oil-cyclosporine mixture will not result in the high efficacy therapeutic agent delivery system as taught herein. In fact adding a low HLB surfactant (Brij) to a castor oil emulsion will result in increasing particle size (see Table 5) causing dramatic increases in free hydrophilic detergent (Lumulse® for example) in the aqueous phase and thus increase eye irritation and reduced drug delivery efficacy.

TABLE 6

| Ingredient | % w/w | % w/w | % w/w | % w/w |
|---|---|---|---|---|
| Castor Oil | 2.5 | 2.5 | 2.5 | 2.5 |
| Lumulse ® GRH-40 | 1.0 | 1.5 | 1.0 | 1.5 |
| BRIJ 72 | | | 0.5 | 0.5 |
| Boric Acid | 0.6 | .0.6 | 0.6 | 0.6 |
| Sodium Borate decahydrate | 0.07 | 0.07 | 0.07 | 0.07 |
| NaCl | 0.37 | 0.37 | 0.37 | 0.37 |
| PEG 400 | 0.4 | 0.4 | 0.4 | 0.4 |
| PHMB | 0.001 | 0.001 | 0.001 | 0.001 |
| Particle size (µm) | 1.08 | 0.16 | 1.14 | 4.23 |

To test cyclosporine delivery efficacy of compositions made in accordance with the teachings herein using methods known to those skilled in the art. Five test emulsions were prepared and administered to the eyes of New Zealand white rabbits. The animals were treated at 1 drop per hour for four hours with manually forced blinking for 10 minutes after each drop instilled into the eye. The corneal and conjunctive cyclosporine A concentrations were evaluated at 20 minutes after the last instillation.

Table 7 demonstrates the superior delivery of test solutions 1, 2 and 3 as compared with the cyclosporine containing and the commercial embodiment, column 5 (the Commercial Castor Oil used in the comparisons expressed here was Restasis® a product and trademark of Allergan, Inc., Irvine, Calif.). Table 6a similarly presents data for test emulsions 4 and 5. Emulsion 4 contains 50% more sesame oil, Lumulse® GRH-25, Brij 93 than emulsion 5, other ingredients are identical. All concentrations in tables 6 and 6a are expressed in weight/weight percent Note that the lower concentration of Brij 93 in emulsion 5 results in an increase in cyclosporine delivery to the cornea (even though the ration of Brij 93 to sesame oil remained constant at 0.12). Tissue levels increased significantly using sesame oil/Brij 93 as the basis for the emulsions. The experimentally measured cyclosporine concentrations in the rabbit conjunctiva and cornea tissue are listed in table 6 were normalized for tissue weight.

TABLE 7

| Ingredients | Control Solution | Test Solution #1 | Test Solution #2 | Test Solution #3 | Restasis ® |
|---|---|---|---|---|---|
| Cyclosporine A (CsA) | 0.05 | 0.05 | 0.05 | 0.05 | 0.05 |
| Castor Oil | 1.25 | | | | 1.25 |
| Sesame Oil | | 1.25 | 1.25 | 1.25 | |
| Lumulse ® GRH-40 | 1 | | | | |
| Lumulse ® GRH-25 | | 0.5 | 0.5 | 0.5 | |
| BRIJ 93 | | 0.05 | 0.1 | 0.25 | |
| Boric Acid | 0.6 | 0.6 | 0.6 | 0.6 | |
| Sodium borate decahydrate | 0.035 | 0.07 | 0.07 | 0.07 | |
| NaCl | 0.35 | 0.37 | 0.37 | 0.37 | |
| KCl | 0.14 | | | | |
| Sodium Chlorite | 0.008 | | | | |
| PHMB | | 0.001 | 0.001 | 0.001 | |
| Water | Q.S. | Q.S. | Q.S. | Q.S. | |

TABLE 7-continued

| Ingredients | Control Solution | Test Solution #1 | Test Solution #2 | Test Solution #3 | Restasis ® |
|---|---|---|---|---|---|
| Brij 93/oil (g/g) | 0 | 0.04 | 0.08 | 0.2 | 0 |
| CsA/Conjunctiva (µg/g) | 0.52 | 0.90 | 0.91 | 0.78 | 0.46 |
| CsA/Cornea (µg/g) | 0.98 | 3.97 | 2.27 | 1.50 | 0.99 |
| Increased[1] delivery to Conjunctive | 13% | 96% | 98% | 70% | 0% |
| Increased delivery to Cornea | −1% | 291% | 129% | 52% | 0% |

[1]Increase delivery of CsA relative to Restasis ®

TABLE 7a

| Ingredients | Control Solution | Test Solution #4 | Test Solution #5 | Restasis ® |
|---|---|---|---|---|
| Cyclosporine A (CsA) | 0.05 | 0.05 | 0.05 | 0.05 |
| Castor Oil | 1.25 | | | 1.25 |
| Sesame Oil | | 1.25 | 0.83 | |
| Lumulse ® GRH-40 | 1 | | | |
| Lumulse ® GRH-25 | | 0.5 | 0.33 | |
| BRIJ 93 | | 0.15 | 0.1 | |
| Boric Acid | 0.6 | 0.6 | 0.6 | |
| Sodium borate decahydrate | 0.035 | 0.08 | 0.08 | |
| NaCl | 0.35 | 0.37 | 0.37 | |
| KCl | 0.14 | | | |
| Sodium Chlorite | 0.008 | | | |
| PHMB | | 0.001 | 0.001 | |
| Water | Q.S. | Q.S. | Q.S. | |
| Brij 93/oil (g/g) | 0 | 0.04 | 0.08 | 0 |
| CsA/Conjunctiva (µg/g) | 0.52 | 0.93 | 0.93 | 0.46 |
| CsA/Cornea (µg/g) | 0.98 | 1.45 | 2.26 | 0.99 |
| Increased[2] delivery to Conjunctive | 13% | 102% | 102% | 0% |
| Increased delivery to Cornea | −1% | 46% | 128% | 0% |

[2]Increase delivery of CsA relative to Restasis ® a registered Trademark of Allergan, Inc. Irvine, CA.

It should be noted here that the present inventor surprisingly observed that therapeutic-containing ophthalmic emulsion solutions made in accordance with the teachings herein are significantly more effective at delivering a hydrophobic therapeutic composition to the eye's surface than Restasis®. Without wishing to be bound by the theory the present inventors proposes that the observed superiority in cyclosporine delivery to the eye can be explained by reference to FIG. 1. Note that in FIG. 1 the hydrophobic drug is localized near the perimeter of the oil particle and is thus more immediately and easily transferred to the eye's surface than in the prior art composition where, as depicted in FIG. 1 the hydrophobic therapeutic is sequestered near the particle's inner core.

Table 8 depicts concentration ranges for selected emulsions ingredients made in accordance with the teachings herein. All values are given in weight/weight percents of the total emulsion weight. In one embodiment of the oil-in-water emulsions made in accordance with the teaching herein the concentration of low HLB to non-polar oil can be expressed as a ratio. Expressed in this manner the ratio of low HLB surfactant/non-polar oil is from approximately 0.002 to 4.0, preferably 0.02 to 0.4.

Table 9 represents a specific formulation that is useful in treating dye eye in accordance with the teachings herein.

TABLE 8

| Ingredient | Concentration range % w/w | Preferred Range % w/w |
|---|---|---|
| Non-polar Oil | 0.5 to 3.0 | 1 to 1.5 |
| [3]Cyclosporine A | 0.01 to 0.15 | 0.02 to 0.06 |
| High HLB Surfactant | 0.1-5.0 | 0.5 to 1.5 |
| Low HLB Surfactant | 0.1-3.0 | 0.1 to 0.5 |
| Water | Q.S. | Q.S. |

[3]The amount of cyclosporine A used in the ophthalmic compositions described here in is an amount that is effective to treat or relieve symptoms associated with dry eye.

TABLE 9

| Ingredient | % w/w |
|---|---|
| Cyclosporine A | 0.05 |
| Sesame oil | 1.25 |
| Lumulse ® GRH-25 | 0.5 |
| Brij 93 | 0.2 |
| Boric Acid | 0.6 |
| Sodium borate decahydrate | 0.07 |
| NaCl | 0.37 |
| PHMB | 0.001 |
| Water for Injection | Q.S. |

Example 3

Artificial Tears

The surprisingly the non-irritating ophthalmic solutions described herein are useful as artificial tears. Artificial tears are lubricant eye drops used to treat the dryness and irritation associated with deficient tear production and dry eyes. They are also used to moisten contact lenses, in eye examinations and to relieve periodic dryness and eye irritation brought on by environmental exposure. Generally artificial tears are isotonic solutions that may contain physiologically acceptable excipients such as demulcents including, for example carboxymethyl cellulose, hydroxypropyl methylcellulose and hyaluronan (also called hyaluronic acid or hyaluronate) (and their respective salts and esters), water, salts, preservatives, viscosity modifiers, tonicity enhancers and other and polymers but generally lack the proteins found in natural tears. The present inventor has discovered that a particularly useful embodiment of the present teaching provides an artificial tears oil-in-water emulsion formulation that is non-irritating and supplies the eye with a natural omega-3 fatty acid in addition to rehydrating the eye surface.

Table 10 provides a non-limiting last of common ingredients used in the non-irritating oil-in-water emulsions as described herein:

| Ingredient | Concentration Range % w/w | Preferred Range % w/w |
|---|---|---|
| Non-polar[4] oil | 0.05-5.0 | 1 to 3.0 |
| hydrophilic surfactant (HLB 8-25) | 0.1 to 5.0 | 0.5 to 1.5 |
| hydrophobic surfactant (HLB <8-3) | 0.1 to 3.0 | 0.1 to 0.5 |
| Demulcent | 0 to 1.0 | |
| Viscosity modifier | 0 to 1.0 | |
| Antioxidant | 0 to 0.5 | |
| Preservative | As needed[5] | |
| Tonicity Adjusting Reagent | As needed | |
| Buffered salts solution | Q.S. | |

[4]As used herein, "non-polar" is understood to refer to oils lacking alkyl side chains having pendent polor group such as hydroxyl groups. A common example of a "polar oil" expressly excluded is castor oil. Mineral oils, although technically non-polar, are excluded from the present compositions. Only plant or animal derived oils are considered within the scope of the present disclosure and appended claims.

[5]Preservative concentration varies with the agent used. The amount of preservative necessary is determined by one skilled in the art of formulation science and is that amount that inhibits microbial growth without affecting the safety and efficacy of the ophthalmic composition and does not irritate the user's eyes.

Representative non-polar oils include but are not limited to omega-3 and 6/9 fatty acids including but not limited to sesame oil, cherry kernel oil, pumpkin seed oil, hemp seed oil, flax seed oil, perilla seed oil, blackcurrant seed oil, cod liver oil, salmon oil, anchovy oil and tuna oil.

In one embodiment the viscosity modifying agent or demulcent are selected from the group consisting of hyaluronic acid and salts thereof, polyvinylpyrrolidone (PVP), cellulose polymers, including hydroxypropyl methyl cellulose (HPMC), hydroxyethyl cellulose (HEC), ethyl hydroxyethyl cellulose, hydroxypropyl cellulose, methyl cellulose and carboxymethyl cellulose (CMC), dextran 70, gelatin, glycerine, polyethylene glycols, polysorbate 80, propylene glycol, povidone, carbomers (e.g. Carbopol®), polyvinyl alcohol, alginates, carrageenans, and guar, karaya, agarose, locust bean, tragacanth and xanthan gums.

In another embodiment a, antimicrobial preservative is added. Preservatives include, but are not limited to polymeric quaternary amine preservatives selected from the group consisting of poly[dimethylimino-w-butene-1,4-diyl] chloride, alpha-[4-tris(2-hydroxyethyl)ammonium]dichloride (Polyquaternium 1®), poly(oxyethyl(dimethyliminio) ethylene dmethyliminio)ethylene dichloride (WSCP®), and polyhexamethylene biguanide (PHMB). The antimicrobial preservatives used in accordance with the teachings herein are present in the liquid aqueous medium in concentrations in the range of about 0.00001% to about 0.01% (w/v), and more preferably in concentrations in the range of about 0.00005% to about 0.001% (w/v) and most preferably in concentrations in the range of about 0.00005% to about 0.0005% (w/v).

Additional antimicrobial components suitable for use herein include and stabilized chlorine dioxide (SCD) (Purogene® is a trademark of BioCide International, Inc. Norman, Okla., U.S.A.). If a chlorine dioxide precursor in included effective preservative or disinfecting concentrations usually are in the range of about 0.002 to about 0.06% (w/v). The chlorine dioxide precursors may be used in combination with other antimicrobial components, such as biguanides, biguanide polymers, salts thereof and mixtures thereof.

Buffers, tonicity modifiers (osmolality adjusting reagents) and other compounds can be added as needed and are described in detail elsewhere. One particularly useful, non-limiting artificial tear formulation is provided in Table 11.

TABLE 11

| Ingredient | % w/w |
| --- | --- |
| Flax Seed Oil | 2.5 |
| Lumulse ® GRH-25 | 1.1 |
| Brij 93 | 0.5 |
| Boric Acid | 0.6 |
| Sodium borate decahydrate | 0.09 |
| NaCl | 0.46 |
| PEG 400 | 0.4 |
| Ascorbic Acid | 0.2 |
| PHMB | 0.0007 |

Formulations

The preparation of the oil-in-water emulsions for the present dry eye-treating compositions is generally as follows. Non-emulsifying agents which are water soluble components, including any water-soluble polymer demulcent(s), are dissolved in the aqueous (water) phase and oil-soluble components including the emulsifying agents are dissolved in the oil phase. The two phases (oil and water) are separately heated to an appropriate temperature. This temperature is the same in both cases, generally a few degrees to 5 to 10 degrees above the melting point of the highest melting ingredients in the case of a solid or semi-solid oil or emulsifying agent in the oil phase. Where the oil phase is liquid at room temperature, a suitable temperature is determined by routine experimentation with the melting point of the highest melting ingredients in the aqueous phase. In cases where all components of either the oil or water phase are soluble in their respective phase at room temperature, no heating may be necessary. The temperature must be high enough that all components are in the liquid state but not so high as to jeopardize the stability of the components. A working temperature range is generally from about 20° C. to about 70° C. To create an oil-in-water emulsion, the final oil phase is gently mixed into either an intermediate, preferably de-ionized water (DI water) phase, or the final aqueous phase to create a suitable dispersion and the product is allowed to cool with or without stirring. In the case wherein the final oil phase is first gently mixed into an intermediate water phase, this emulsion concentrate is thereafter mixed in the appropriate ratio with the final aqueous phase. The final aqueous phase includes the water soluble polymer as well as other aqueous-soluble components. In such cases, the emulsion concentrate and the final aqueous phase need not be at the same temperature or heated above room temperature, as the emulsion has already been formed at this point.

Semisolids may form in the process of self-emulsification if the amount of ethylene oxide units in one emulsifier is too large. Generally, if the surfactant or surfactants have more than 10 ethylene oxide units in their structures, the surfactant and oil phase is mixed with a small amount of the total composition water, e.g., about 0.1-10%, to first form a semi-solid substance in the form of a paste, which is thereafter combined with the remaining water. Gentle mixing may then be required until the hydrated emulsifiers are fully dissolved to form the emulsion.

In one embodiment, the surfactant and oil are initially combined and heated. A small amount of the aqueous phase is then added to the oil phase to form a semi-solid substance in the form of a paste. Paste is defined here as a semisolid preparation which does not flow. The amount of the aqueous phase added may be from 0.1-10 fold, preferably from 0.5 to 5 fold and most preferably 1-2 fold. After the paste is formed, additional water is added to the paste at the same temperature as above. In some embodiments, the amount of water added is 5-20 fold. The emulsion is then gently mixed. In some embodiments, mixing may occur for 30 minutes to 10 hours.

In a preferred embodiment, the particles are then sized. A Horiba LA-920 particle size analyzer may be used according to the manufacturer's instructions for this purpose. In a preferred embodiment, the particles are between 0.08 and 0.18 microns in size before passing to the next step.

In the next step, the particles may be mixed with other aqueous components such as water, one or more demulcents and buffer (preferably boric acid based). Optionally, electrolytes, such as calcium chloride dihydrate, magnesium chloride hexahydrate, potassium chloride and sodium chloride, and Kollidon 17 NF may be added. While the electrolytes are not necessary to form the emulsions, they are very helpful to preserve ocular tissue integrity by maintaining the electrolyte balance in the eye. Likewise, the buffer is not critical, but a boric acid/sodium borate system is preferred in one embodiment of the invention because a phosphate-based buffer system will precipitate with the preferred electrolytes.

The pH is adjusted to 6.8-8.0, preferably from about 7.3 to 7.7. This pH range is optimal for tissue maintenance and to avoid ocular irritation. A preservative may then be added. In a preferred embodiment, stabilized chlorine dioxide (SCD) (Purogene®) material is added as preservative.

The oil-in-water emulsions described herein can be sterilized after preparation using autoclave steam sterilization or can be sterile filtered by any means known in the art. Sterilization employing a sterilization filter can be used when the emulsion droplet (or globule or particle) size and characteristics allows. The droplet size distribution of the emulsion need not be entirely below the particle size cutoff of the sterile filtration membrane to be sterile-filterable. In cases where the droplet size distribution of the emulsion is above the particle size cutoff of the sterile filtration membrane, the emulsion needs to be able to deform or acceptably change while passing through the filtrating membrane and then reform after passing through. This property is easily determined by routine testing of emulsion droplet size distributions and percent of total oil in the compositions before and after filtration. Alternatively, a loss of a small amount of larger droplet-sized material may be acceptable.

The emulsions described herein are generally non-aseptically filtered through a clarification filter before sterile filtration or aseptically clarify-filtered after autoclave steam sterilization. In a preferred embodiment, the emulsion is filter sterilized using a 0.22 micron filter. Preferably, 98-99% of the emulsion should pass through the 0.22 micron filter. Note that particles larger than 0.22 micron may pass through by altering their shape temporarily. In a preferred embodiment, the material is then tested to verify the effectiveness of the sterilization step. Storage is preferably below 25° C. in order to maintain stability. Thereafter, the emulsions are aseptically filled into appropriate containers.

Compositions according to the teachings herein may be used in methods which comprise administering the composition to an eye of a subject (human or animal), in an amount effective in providing a desired therapeutic effect to the subject. Such therapeutic effect may be an ophthalmic therapeutic effect and/or a therapeutic effect directed to one or more other parts of the subject's body or systemically to the subject's body. In preferred embodiments, the therapeutic effect is treatment and/or relief from symptoms of dry eye.

The aqueous phase or component and the oil phase and component used in accordance with the present invention are selected to be effective in the present compositions and to have no substantial or significant deleterious effect, for example, on the compositions, on the use of the compositions, on the contact lens being treated, on the wearer of the treated lens, or on the human or animal in whose eye the present composition is placed.

The liquid aqueous medium or component of the present compositions preferably includes a buffer component which is present in an amount effective to maintain the pH of the medium or aqueous component in the desired range. The present compositions preferably include an effective amount of a tonicity adjusting component to provide the compositions with the desired tonicity.

The aqueous phase or component in the present compositions may have a pH which is compatible with the intended use, and is often in the range of about 4 to about 10. A variety of conventional buffers may be employed, such as phosphate, borate, citrate, acetate, histidine, tris, bis-tris and the like and mixtures thereof. Borate buffers include boric acid and its salts, such as sodium or potassium borate. Potassium tetraborate or potassium metaborate, which produce boric acid or a salt of boric acid in solution, may also be employed. Hydrated salts such as sodium borate decahydrate can also be used. Phosphate buffers include phosphoric acid and its salts; for example, $M_2HPO_4$ and $MH_2PO_4$, wherein M is an alkali metal such as sodium and potassium. Hydrated salts can also be used. In one embodiment described herein, $Na_2HPO_4 \cdot 7H_2O$ and $NaH_2PO_4 \cdot H_2O$ are used as buffers. The term phosphate also includes compounds that produce phosphoric acid or a salt of phosphoric acid in solution. Additionally, organic counter-ions for the above buffers may also be employed. The concentration of buffer generally varies from about 0.01 to 2.5 w/v % and more preferably varies from about 0.05 to about 0.5 w/v %.

The type and amount of buffer are selected so that the formulation meets the functional performance criteria of the composition, such as surfactant and shelf life stability, antimicrobial efficacy, buffer capacity and the like factors. The buffer is also selected to provide a pH, which is compatible with the eye and any contact lenses with which the composition is intended for use. Generally, a pH close to that of human tears, such as a pH of about 7.45, is very useful, although a wider pH range from about 6 to about 9, more preferably about 6.5 to about 8.5 and still more preferably about 6.8 to about 8.0 is also acceptable. In one embodiment, the present composition has a pH of about 7.0.

The osmolality of the present compositions may be adjusted with tonicity agents to a value which is compatible with the intended use of the compositions. For example, the osmolality of the composition may be adjusted to approximate the osmotic pressure of normal tear fluid, which is equivalent to about 0.9 w/v % of sodium chloride in water. Examples of suitable tonicity adjusting agents include, without limitation, sodium, potassium, calcium and magnesium chloride; dextrose; glycerin; propylene glycol; mannitol; sorbitol and the like and mixtures thereof. In one embodiment, a combination of sodium chloride and potassium chloride are used to adjust the tonicity of the composition.

Tonicity agents are typically used in amounts ranging from about 0.001 to 2.5 w/v %. These amounts have been found to be useful in providing sufficient tonicity for maintaining ocular tissue integrity. Preferably, the tonicity agent(s) will be employed in an amount to provide a final osmotic value (expressed in osmolality) of 150 to 450 mOsm/kg, more preferably between about 250 to about 330 mOsm/kg and most preferably between about 270 to about 310 mOsm/kg. The aqueous component of the present compositions more preferably is substantially isotonic or hypotonic (for example, slightly hypotonic, e.g., about 240 mOsm/kg) and/or is ophthalmically acceptable. In one embodiment, the compositions contain about 0.14 w/v % potassium chloride and 0.006 w/v % each of calcium and/or magnesium chloride.

In addition to tonicity and buffer components, the present compositions may include one or more other materials, for example, as described elsewhere herein, in amounts effective for the desired purpose, for example, to treat contact lenses and/or ocular tissues, for example, to provide a beneficial property or properties to contact lenses and/or ocular tissues, contacted with such compositions. In one embodiment anti-oxidants are added to preserve the solutions' stability as well as to reduce ocular surface free radial damage. Suitable non-limiting examples include vitamin C, vitamin E, vitamin A and butylhydroxytoluene (BHT).

Packaging can be in multi-use vials with a preservative, or single use vials without (although not intended as a limitation as to packaging form or function). Additionally, packaging may be conducted using a nitrogen gas flush to prevent or reduce product exposure to atmospheric oxygen and thus preserve product shelf life.

In one embodiment, the compositions include a second therapeutic agent in addition to the water-soluble polymer for treatment of dry eye. The compositions described herein are useful, for example, as a carrier or vehicle, for the delivery of at least one additional therapeutic agent to or through the eye. Any suitable therapeutic component may be included in the present compositions provided that such therapeutic component is compatible with the remainder of the composition, does not unduly interfere with the functioning and properties of the remainder of the composition, is effective, for example, to provide a desired therapeutic effect, when delivered in the present composition and is effective when administered to or through the eye. For example, in a very useful embodiment, the delivery of hydrophobic therapeutic components or drugs to or through the eye may be accomplished.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. An ophthalmic oil-in-water emulsion composition comprising: an ophthalmically acceptable omega-3 fatty acid-containing oil, wherein the oil is from a botanical source selected from the group consisting of Chia, Kiwifruit, Perilla (shiso or Perilla frutescens), Flax seed, Lingonberry, Camelina, Purslane and Black Raspberry, or is an oil from cold water fish selected from the group consisting of cod liver oil, salmon oil, anchovy oil and tuna oil; a hydrophilic surfactant selected from the group consisting of polyethylene glycol esters of hydrogenated castor oil; a hydrophobic non-co-block surfactant from the group consisting of a polyoxyethylene(2) stearyl ether and a polyoxyethylene(2) oleyl ether; and water; and wherein said oil-in-water emulsion composition has an average particle size less than 1 μm in diameter.

2. The composition according to claim 1 wherein said hydrophilic surfactant and said hydrophobic non-co-block surfactant are present in a ratio of 10.0 to 4.9.

3. The composition according to claim 1 wherein said hydrophilic surfactant and said hydrophobic non-co-block surfactant are present in a ratio of 14.5 to 4.9.

4. The composition according to claim 1 wherein said hydrophilic surfactant and said hydrophobic non-co-block surfactant are present in a ratio of 10.0 to 2.0.

5. The composition according to claim 1 wherein said hydrophilic surfactant and said hydrophobic non-co-block surfactant are present in a ratio of 14.5 to 2.0.

6. The composition according to claim 1 wherein said omega-3 fatty acid-containing oil is from a botanical source selected from the group consisting of Chia, Kiwifruit, Perilla (shiso or Perilla frutescens) Flax seed, Lingonberry, Camelina, Purslane and Black Raspberry.

7. The composition according to claim 1 wherein said omega-3 fatty acid-containing oil is an oil from cold water fish selected from the group consisting of cod liver oil, salmon oil, anchovy oil and tuna oil.

8. The composition according to claim 1 further comprising excipients selected from the group consisting of buffers, microbicides, demulcents, viscosity modifying agents, metal salts, emulsion stabilizers and therapeutic agents.

9. An ophthalmic oil-in-water emulsion composition comprising: at least one ophthalmically acceptable omega-3 fatty acid-containing oil, wherein the oil is from a botanical source selected from the group consisting of Chia, Kiwifruit, Perilla (shiso or Perilla frutescens), Flax seed, Lingonberry, Camelina, Purslane and Black Raspberry, or is an oil from cold water fish selected from the group consisting of cod liver oil, salmon oil, anchovy oil and tuna oil; a hydrophilic surfactant selected from the group consisting of polyethylene glycol esters of hydrogenated castor oil; and a hydrophobic non-co-block surfactant selected from the group consisting of a polyoxyethylene(2) stearyl ether and a polyoxyethylene(2) oleyl ether, wherein the composition has an average particle size of less than 0.6 μm.

10. An ophthalmic oil-in-water emulsion composition consisting essentially of: water; at least one ophthalmically acceptable omega-3 fatty acid-containing oil, wherein the oil is from a botanical source selected from the group consisting of Chia, Kiwifruit, Perilla (shiso or Perilla frutescens), Flax seed, Lingonberry, Camelina, Purslane and Black Raspberry, or is an oil from cold water fish selected from the group consisting of cod liver oil, salmon oil, anchovy oil and tuna oil; a hydrophilic surfactant selected from the group consisting of polyethylene glycol esters of hydrogenated castor oil; and a hydrophobic non-co-block surfactant selected from the group consisting of a polyoxyethylene(2) stearyl ether and a polyoxyethylene(2) oleyl ether, wherein the composition has an average particle size of less than 0.6 μm.

11. An ophthalmic oil-in-water emulsion composition consisting essentially of water, flax seed oil, a polyethylene glycol ester of hydrogenated castor oil, and a polyoxyethylene(2) oleyl ether, wherein the composition has an average particle size of less than 0.6 μm.

12. An ophthalmic oil-in-water emulsion composition consisting essentially of water, flax seed oil, a polyethylene glycol ester of hydrogenated castor oil, a polyoxyethylene(2) stearyl ether or a polyoxyethylene(2) oleyl ether, and an amount of cyclosporine A effective to relieve dry eye symptoms, wherein the composition has an average particle size of less than 0.6 μm.

* * * * *